(12) United States Patent
Aluja-Schuneman et al.

(10) Patent No.: US 6,555,120 B1
(45) Date of Patent: Apr. 29, 2003

(54) ISOLATION, STRUCTURAL DETERMINATION, SYNTHESIS, BIOLOGICAL ACTIVITY AND APPLICATION AS CONTROL AGENT OF THE HOST MARKING PHEROMONE (AND DERIVATIVES THEREOF) OF THE FRUIT FLIES OF THE TYPE ANASTREPHA (DIPTERA: TEPHRITIDAE)

(75) Inventors: Martin Ramon Aluja-Schuneman, Coatepec (MX); Francisco Diaz-Fleischer, Tapachula (MX); Andrew J. F. Edmunds, Therwil (CH); Leonhard Hagmann, Therwil (CH)

(73) Assignee: Instituto de Ecologia, A.C., Veracruz (MX)

( * ) Notice: Subject to any disclaimer, the term of this patent is extended or adjusted under 35 U.S.C. 154(b) by 0 days.

(21) Appl. No.: 09/830,282
(22) PCT Filed: Oct. 21, 1999
(86) PCT No.: PCT/MX99/00030
§ 371 (c)(1), (2), (4) Date: Jul. 25, 2001
(87) PCT Pub. No.: WO00/22924
PCT Pub. Date: Apr. 27, 2000

(30) Foreign Application Priority Data

Oct. 21, 1998 (MX) ................................. 988732

(51) Int. Cl.[7] ..................... A01N 25/00; C07C 229/00
(52) U.S. Cl. ..................... 424/405; 562/571; 554/110
(58) Field of Search ........................... 562/571; 424/405

(56) References Cited

U.S. PATENT DOCUMENTS 3,758,525 A * 9/1973 Yoshida et al.

* cited by examiner

Primary Examiner—Johann Richter
Assistant Examiner—Paul A. Zucker
(74) Attorney, Agent, or Firm—Timothy J. Keefer; Wildman, Harrold, Allen & Dixon

(57) ABSTRACT

The 2-(2,14-Dimethyl-pentadecanoylamin)-pentanedioic acid (I) and compounds of the formula (II),

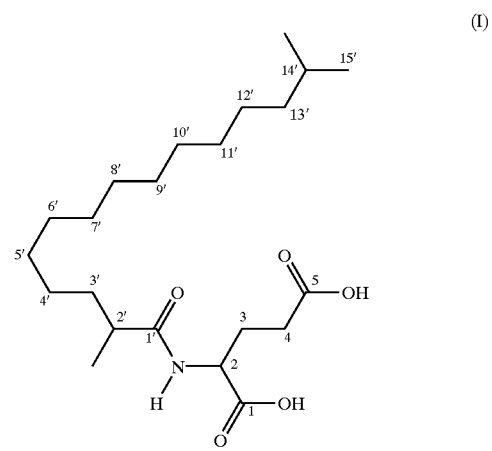

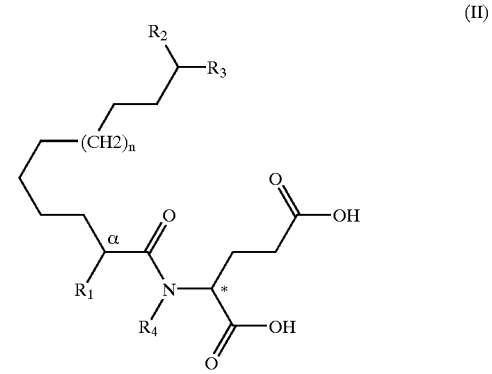

wherein the substituents have the meaning disclosed in the specification, are used as oviposition deterring pheromones against the following fruit flies (Diptera: Tephritidae) of economical importance: *Anastrepha fraterculus* (south America fruit fly), *A. grandis*, *A. ludens* (Mexican fruit fly), *A. obliqua* (mango fly), *A. serpentina* (sapodilla fly), *A. striata* (guayabi fly) and *A. suspensa* (Caribbean fruit fly). The above-mentioned substances, if conveniently formulated, can be used to reduce the damage caused by these insects to fruits which are cultivated in commercial and semi-commercial orchards, in garden orchards and in isolated trees in residential gardens.

15 Claims, No Drawings

ISOLATION, STRUCTURAL DETERMINATION, SYNTHESIS, BIOLOGICAL ACTIVITY AND APPLICATION AS CONTROL AGENT OF THE HOST MARKING PHEROMONE (AND DERIVATIVES THEREOF) OF THE FRUIT FLIES OF THE TYPE ANASTREPHA (DIPTERA: TEPHRITIDAE)

REFERENCE TO RELATED APPLICATIONS

The present application corresponds to the U.S. national phase of PCT/MX99/00030 based on Mexican patent application MX988732 filed on Oct. 21, 1998.

FIELD

This invention is related to host marking pheromones (HMPs) also known as oviposition deterring pheromones (ODPs) in insects. In particular it refers to host marking pheromones in fruit flies of the genus Anastrepha.

BACKGROUND

Fruit flies (Diptera: Tephritidae) are considered among the most economically important pests worldwide (Aluja and Liedo 1993; McPheron and Steck 1996). The most notorious pestiferous species belong to the genera Anastrepha, Bactrocera, Ceratitis, Rhagoletis, and Toxotrypana (Aluja 1993). Among the 184 reported species of Anastrepha (Aluja 1994), seven stand out because of the damage they cause to commercially grown fruit: *A. fraterculus, A. grandis, A. ludens, A. obliqua, A. serpentina, A. striata* and *A. suspensa*. Distribution and fruit species attacked are indicated in TABLE 1 (from Hernandez-Ortiz and Aluja 1993).

TABLE 1

Distribution and most common hosts of the seven economically important Anastrepha species.

| Anastrepha species | Distribution | Commercially grown fruit species attacked |
| --- | --- | --- |
| A. fraterculus | Mexico to Argentina | Guava, Oranges |
| A. grandis | South America | Commercially grown cucurbits |
| A. ludens | Southern USA to Costa Rica | Oranges, Mango, Grapefruit |
| A. obligua | Mexico to Argentina | Mango, Tropical Plums |
| A. serpentina | Mexico to Argentina | Mammee Apple, Chico Zapote |
| A. striata | Mexico to Argentina | Guava |
| A. suspensa | Florida and Caribbean Islands | Grapefruit, Guava |

Damage of these fly species is direct (larvae in fruit) and indirect (severe quarantine restrictions that limit international commerce). Infestation level (i.e., percent infested [=lost] fruit in a tree can vary between zero and 90% depending on the fruit growing region, fruit species or cultivar, size of fruit fly population, management intensity in orchard and degree of capitalization of orchard owner. Control of these pests has been historically attempted through fumigants, toxic bait sprays (a food-based bait mixed with-an insecticide) and on occasion by use of the sterile insect technique (SIT) (reviewed by Steiner 1955 and Aluja 1994). Despite being quite effective, the large scale use of toxic bait sprays is no longer acceptable because of the negative impact on beneficial and native entomofauna (Asquith and Messing 1992, Hölmer and Dahlsten 1993 and references therein). In recent years, a number of alternatives such as the use of gibberelic acid to enhance the innate resistance of citrus to fly attack (Greany 1989), insect growth regulators such as cyromazine (Moreno et al. 1994), pathogens such as *Bacillus thuringiensis* Berliner (Martinez et al. 1997) and photoactivated dyes as for example SureDye$^{M.R.}$ (PhotoDye International, Inc., Boca Raton, USA) are being explored. Despite their promise as viable alternatives to toxic bait sprays, some of these methods could still prove unacceptable because of the deleterious effect on nontarget insects (Aluja 1996). The latter, because the killing agent needs to be ingested by the adult insect. The only practical way of achieving this is by mixing it with a food-based bait. As is the case with food-based baits mixed with an insecticide, lures used in combination with photo-activated dyes or insect growth regulators are non-specific. That is, they attract a large, number of nontarget insects (such as many species of insects in the order Diptera) which are also killed.

A highly selective alternative to the use of insecticides that has been recently tested in fruit flies of the genus Rhagoletis, and that does not require a bait to be effective, is the use of synthetic host marking pheromones (HMPs). HMPs are deposited by flies on the surf ace of a fruit after an egglaying bout and given a large enough concentration deter conspecifics from ovipositing in the same fruit (Katsoyannos and Boller 1980). Based on this knowledge and chemical work by Hurter et al. (1987a; 1987b) and Ernst and Wagner (1989), it was possible to successfully test the synthetic HMP of *Rhagoletis cerasi* as a fruit-infestation-reducing-agent in commercial cherry orchards in Switzerland (Aluja and Boller 1992a; 1992b). Application of synthetic HMP to the entire tree crown reduced the number of larvae per kg of fruit by a factor of 10 when compared with an untreated tree (0.226 vs. 0.021 pupae/fruit) in untreated and treated trees, respectively. A significant reduction.in fruit infestation could also be achieved when only one half (top to bottom) of the tree crown was treated (Aluja and Boller 1992b). Of significance here, is the fact that host marking behavior has been also reported in several Anastrepha species: *A. suspensa* (Prokopy et al., 1977), *A. fraterculus* (Prokopy et al. 1982), *A. sororcula* and *A. obliqua* (Simoes et al. 1978), *A. pseudoparallela* (Polloni and Da Silva 1986), *A. striata* (Aluja et al. 1993), *A. bistrigata* (Gomes -Da Silva 1991), *A. grandis* (Selivon 1991) and *A. ludens* (Papaj and Aluja 1993). As was the case with Hurter and collaborators (Hurter et al. 1987b), when working with *R. cerasi*, Santiago and collaborators (1990; 1991) demonstrated that the feces of *A. ludens* and *A. serpentina* contained a HMP. Using thin-layer chromatography, they further showed that one band provoked the deterrent effect. They also were able to show that crude feces extracts of *A. ludens* applied to fruit-bearing mango tree branches, reduced the level of infestation by *A. ludens* (Santiago et al. 1991). In general, host marking pheromones, given a high enough concentration, deter oviposition in fruit by fruit fly females (Averill and Prokopy 1989).

There remains a need in the art for a highly selective (i.e., directed only at flies in the genus Anastrepha) and environmentally-friendly alternative to the use of Anastrepha control methods that is not dependent on a food-based bait to deliver the toxicant or killing agent. The present invention describes several substances that reduce the damage inflicted to fruit of.value to humans by flies in the genus Anastrepha and that does not require a food-based bait to be delivered or to be effective.

SUMMARY

According to the present invention it has been found that 2-(2', 14'-Dimethyl-pentadecanoylamino)-pentanedioic acid of the formula (I),

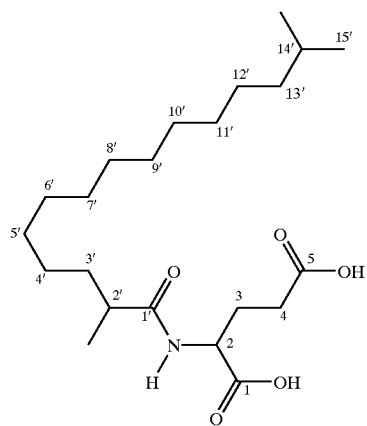

(I)

isolated from the feces of *Anastrepha ludens*, functions as an oviposition deterrent against economically and non-economically important fruit flies (Diptera: Tephritidae) of the genus Anastrepha. This is significant because the above mentioned substance if properly formulated, can henceforth be used to reduce the damage these insects inflict on fruit grown in commercial and semi-commercial orchards, in backyard gardens or in single trees planted in residential gardens. The present invention relates to a method for the isolation of the host marking pheromone (oviposition deterring pheromone) of *Anastrepha ludens* which is applicable to all species of fruit flies of the genus Anastrepha. The invention also relates to a method for the synthesis of oviposition deterrents which have the general formula (II)

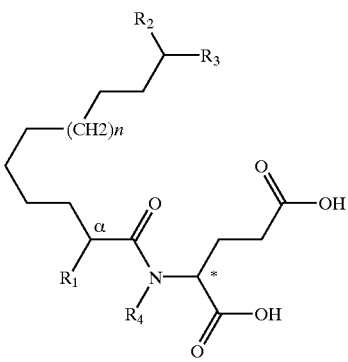

(II)

Where R1 is H, C1–C4 alkyl, C3–C6 cycloalkyl, C3- or C4 alkenyl, C3- or C4 alkynyl;

R2 and R3 independent of one another are H or C1–C4 alkyl, C3–C6 cycloalkyl, C3- or C4 alkenyl, C3- or C4 alkynyl, benzyl or benzyl which is substituted once to three times on the phenyl ring by halogen, C1–C4 alkyl;

R4 is H or C1–C4 alkyl, C3–C6 cycloalkyl, C3- or C4 alkenyl, C3- or C4 alkynyl, C1–C4 alkyl carbonyl, benzyl or benzyl which is substituted once to three times on the phenyl ring by halogen, C1–C4 alkyl, Where α refers to (R) or (S) stereoisomers (or their mixtures), with the premise that R1 is not=H.

Where n=an integer between 0 and 15.

Where * refers to (L) or (D) amino acid stereochemistry (or their mixtures).

The alkyl, alkenyl and alkynyl groups in the above definitions can be straight chain or branched. Alkyl groups for example are methyl, ethyl, n-propyl, isopropyl, n-butyl, sec-butyl, iso-butyl, and tert-butyl.

Examples of alkenyls are vinyl, allyl, methallyl, 1-methylvinyl, but-2-en-1-yl.

The cycloalkyl radicals which are suitable substituents are, for example cyclopropyl, cyclobutyl, cyclopentyl, and cyclohexyl.

Alkyl carbonyl is, for example acetyl, propionyl and pivaloyl.

The invention also relates to the mono- or di-carboxylic acid salts which the compound of formula (II) can form with bases. These salts are for example, alkali metal salts, for example sodium and potassium salts; alkaline earth metal salts, for example calcium and magnesium salts; ammonium salts, i.e. unsubstituted ammonium salts and mono or polysubstituted ammonium salts, for example triethylammonium and methylammonium salts; or salts with other bases.

Preferred alkali metal and alkaline earth metal hydroxides as salt-forming agents are, for example, the hydroxides of lithium sodium, potassium, magnesium or calcium, and in particular those of sodium and potassium.

Examples of amines which are suitable for ammonium salt formation include ammonia and primary, secondary, and tertiary C1–C18 alkyl amines, for example methylamine, ethylamine, n-propylamine, diethylamine, and triethylamine; Preferred is triethylamine.

The possible presence of at least one asymmetric carbon in the compounds of formula (II) means that the compounds can occur in optically active individual isomers and in the form of racemic mixtures. In the present invention, the active compounds of the formula (II) are to be understood as meaning both the pure optical antipodes and the racemates or diastereoisomers.

If an aliphatic C=C double bond is present, geometric isomerism can occur. The present invention also relates to these isomers.

Preferred compounds of the formula (II) have the formula (IIa)

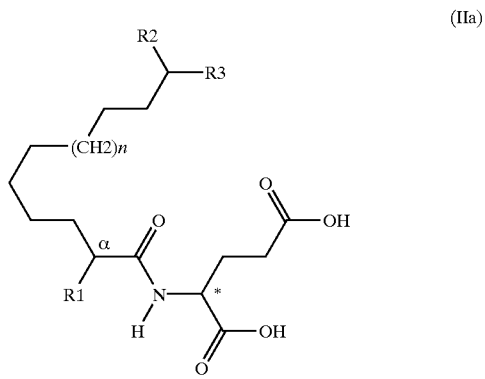

(IIa)

in which R1, R2, R3, n, α and * are as defined under formula (II).

Particularly preferred compounds are those of the formula (IIa) in which R1 is methyl, and n is an integer between 5 and 10.

Compounds which are also especially preferred are those of the formula (IIa) where R2 and R3, independent of one another, are H or methyl.

Compounds which are also especially preferred have (R) or (S) α stereochemistry or are mixtures of α-(R)/(S) isomers.

Compounds which are particularly important have (L) stereochemistry at *.

DETAILED DESCRIPTION OF THE INVENTION

Production and Isolation of the Raw Material (Natural Pheromone)

The raw material was extracted from fly feces of laboratory reared *A. ludens, A. obliqua* and *A. serpentina*. Feces were obtained as follows: In a 30×30×30 cm glass cage, we placed 300 ml of fruit fly pupae (equivalent to ca. 11,000 adult flies). In order to increase the exposed surface to flies, two 13×25 cm glass pieces were introduced into the cage. Each cage was provided with food (sucrose and hydrolyzed protein at a 3:1 ratio) and water. Flies were kept in cages during 30 days. At this time, all living and dead flies were removed. Dried eggs, broken wings, and legs were also removed. The remaining "dirt" (containing mostly fly feces) was then scratched off the glass surfaces with a metal spatula. Each cage yielded ca. 10 g of feces. Fly feces were kept in plastic petri dishes or bottles at −15° C. until further use. To obtain crude pheromonal extracts for purification and biological experimentation batches of 400 g of feces of *Anastrepha ludens* were mixed with 1,000 ml of methanol and sonicated manually for 15 min. After this, the liquid was subjected to centrifugation at 12,000 RPM during 20 min. The supernatant was then concentrated in a rotary evaporator to provide the stock solution for further use.

EXTRACTION, PURIFICATION AND STRUCTURAL ELUCIDATION OF HOST MARKING PHEROMONE (HMP) OF *ANASTREPHA LUDENS*

Extraction and purification procedure of the oviposition deterring, host marking pheromone Extraction 167 g fly feces from *Anastrepha ludens* were suspended in 5 l of ethanol and stirred for 17 hr. at room temperature. The solid material was filtered off, rinsed with 1 l ethanol and the extraction procedure was then repeated once with 2 l ethanol containing 3.5 ml trifluoro-acetic acid. The combined ethanol extracts were concentrated on a rotary evaporator at 50° C. and 20 mbar to almost dryness. After 6 hr. of lyophilization, the residue (33.8 g) was dissolved in 300 ml methanol at 50° C. and cooled down to room temperature. After 2 hr., the precipitated fat (10.5 g) was filtered off and rinsed with methanol. The solution was then evaporated to dryness, giving 23.3 g of a honey-yellow residue which was used in four batches for preparative HPLC.

Purification

Column 1: 50×250 mm, Lichrospher RP-18, 7 $\mu$m (Merck). Flow rate: 0–60 min.: 75 ml/min., 60–90 min.: 100 ml/min. Mobile phase: 0–60 min., linear gradient from 100% water to 100% methanol, 60–90 min.: 100% methanol. The fractions were collected according to peak development of chromatogram. UV-Detection: 220 nm. Electrophysiological activity eluted between 47–60 min. containing 2.43 g of dry matter.

Column 2: 50×250 mm, Kromasil KR100-C18, spher. 7 $\mu$m (Eka Nobel), Flow rate 0–45 min.: 70 ml/min., 45–90 min.: 100 ml/min. Mobile phase: 0–45 min.: linear gradient from 50% acetonitrile in water to 100% acetonitrile. Fractions were collected according to peak development of chromatogram. UV-Detection: 200 nm. Two electrophysiological active regions: (1) 12–18 min., containing 63 mg dry matter, and (2) 36–42 min., containing 28 mg dry matter.

For further investigations, only material from region 1 was purified.

Mobile phases consisted of the following solutions:

A: 100% of water with 0.1% of formic acid.
B: 100% of acetonitrile with 0.1% of formic acid.
Detection: UV at 195 nm.
HPLC columns were supplied by: Macherey-Nagel.

Column 3: 10×250 m, 10 $\mu$m Nucleosil CN 100. Flow rate: 4 ml/min. Injection: 6.3 mg in 1.0 ml of water (10 repetitions). Mobile phase: 0–2 min., 80% A in 20% B; 2–25 min., linear gradient from 80% A in 20% B to 60% A in 40% B; 25–35 min 60% A in 40% B; 35–40 min., linear gradient from 60% A in 40% B to 100% B. Vol. of fractions: 4 ml. Electrophysiological activity in fractions 23–27, evaporated (Rotavap), dissolved in 1 ml of 50% A in 50% B.

Column 4: 10×250 mm, 7 $\mu$m Nucleosil Phenyl 100. Flow rate: 4 ml/min. Injection 200 $\mu$l (5 repetitions). Mobile phase: 0–60 min., 68% A in 32% B. Vol. of fraction: 4 ml. El. act. in fractions 36–42, evap. and dissolved in 5 ml of 50% A in 50% B.

Column 5: 10×250 mm, 7 $\mu$m Nucleosil C-18 100. Flow rate: 4 ml/min. Injection 1 ml (5 repetitions). Mob. phase: 0–60 min. 65% A in 35% B. Vol. of fractions: 4 ml. El. act. in fractions 34–40, evap. and dissolved in 1.0 ml of 50% A in 50% B.

Column 6: 4×250 mm, 7 $\mu$m Nucleosil OH (Diol) 100. Flow rate: 1.0 ml/min. Injection: 200 $\mu$l (5 repetitions). Mobile phase: 0–70 min., 65% A-in 35% B. Vol. of fraction: 1.0 ml. El. phys. act. in fractions 9–11, evap. and dissolved in 1.0 ml of 50% A in 50% B.

Column 7: 4×250 mm, 5 $\mu$m Nucleosil C-18 AB 100. Flow rate: 1.0 ml/min. Injection: 250 $\mu$l (4 repetitions). Mobile phase: 0–70 min., 65% A in 35% B. Vol. of fraction: 1.0 ml. El. phys. act. fractions 49–52 combined and evap. to dryness for structural analysis.

Structure elucidation of the oviposition deterring, host marking pheromone

Mass Spectroscopy

FAB-MS gives strong molecular ions at m/z 400 (MH$^+$) and 422 (M Na$^+$) this corresponds to a molecular weight of 399 for the pheromone. The exact mass has been determined by high resolution MS to 422.2864 for M+Na, and the molecular formula could be deduced to $C_{22}H_{41}NO_5$ for the pheromone with a difference of 1–8 uma from calculated to observed mass.

The pheromone has been esterified with diazomethane giving a molecular ion at m/z 428 (MH$^+$, APCI-MS). The difference of 28 mass units indicates the presence of two methylated carboxyl groups. Characteristic fragmentations are observed for the molecular ion in the MS-MS mode. All of the recorded fragments can be assigned to specific cleavages (relative intensities in % of the base peak). 428(77), 396(31), 368(8), 336(1), 253(6), 225(5) 183(2), 176(100), 169(6), 158(45) 155(4), 144(42), 141(4), 127(6), 116(19), 113(4), 99(4), 98(17), 85(3), 71(4), 57(4), 43(1).

NMR Data.

Chemical shifts of the isolated natural pheromone in ppm, 500 MHz, in CDCl$_3$:

| Carbon No. | Carbon shifts | Multiplicities | Proton shifts |
|---|---|---|---|
| 1 | 176.8 | COOH | — |
| 2 | 51.3 | $CH_2$ | 4.67 br. |
| 3 | 26.5 | $CH_2$ | 4.67 br. 2.25 br. |
| 4 | 29.4 | CH | 2.53 br. |
| 5 | 178.8 | COOH | — |
| — | — | NH | 6.26 br. |
| 1' | 177.2 | CONH | — |
| 2' | 41.3 | CH | 2.28 br. |
| 3' | 34.3 | $CH_2$ | 1.63, 1.41 br. |
| 4'–12' | 29.9, 29.7 (2x), 29.5, 29.2, 29.0, 28.8, 27.4, 27.2 | $CH_2$ | 1.25–1.26 br. |
| 13' | 39.0 | $CH_2$ | 1.14 br. |
| 14' | 27.9 | CH | 1.51 m |
| 15', 14'-Me | 22.7 | $CH_3$ | 0.86 d |
| 2'-Me | 17.7 | $CH_3$ | 1.15 d |

The NMR signals in methanolic solvents are markedly sharper. The chemical shifts of the natural pheromone in $CDCl_3/CD_3OD$ 1:1 are:

$^1$H-NMR: 7.60 (s, 1 NH), 4.36 (dd, 1H), 2.32 (m, 2H), 2.27 (m, 1H), 2.11 (m, 1H), 1.88 (m, 1H), 1.52 (m, 1H), 1.42 (m, 1H), 1.29 (m, 1H), 1.18 (br., 18H), 1.07 (q, 2H), 1.03 (d, 3H), 0.77 (d, 6H).

$^{13}$C-NMR($CDCl_3$=77.0 ppm): 177.99, 175.04, 173.5, 51.18, 40.45, 38.49, 33.56, 29.76, 29.29, 29.05, 29.00 (4x), 28.89, 27.34, 26.84, 26.76, 26.32, 21.71 (2x), 16.67.

Proton and carbon connectivities are based on two-dimensional NMR experiments (COSY, HCCORR, HMBC, ROESY,).

Chirality Determination of the Amino Acid Moiety

The acid hydrolyzed natural pheromone has been derivated to the N-trifluoroacetyl glutamic acid isopropylester. On the chiral GC column (Chirasil-L-Val), the L-isomer showed a retention time of 25.6 min., the D-isomer 24.2 min. based on the synthetic compounds. Temperature program: 70° C. (3 min. isocratic), 2° C./min. to 190°. The sample of the chromatographically purified natural product consisted of 21% D-glutamic acid and 79% L-glutamic acid which has been confirmed by co-injection of the natural and synthetic sample.

Chirality Determination of the α-methyl Fatty Acid Moiety

The four possible stereoisomers can be described as R-L, S-L, R-D, S-D, in which R and S describe the chirality of the α-methyl fatty acid, whereas L and D indicate the chirality of the glutamic acid.

The total synthesis of all four possible isomers has been achieved via stereoselective routes analogous-to literature procedures as described below. The two diastereomeric pairs of enantiomers can be distinguished under specific HPLC conditions (Nucleosil-100-7um-Phenyl, 10×250 mm, 4 ml/min, 40% acetonitrile/60% water, 0.1% formic acid, 195 nm UV detection). The retention time for R-L and S-D was 46 min. whereas R-D and S-L had 48 min. The natural pheromone eluted after 46 min. Since the amino acid configuration of the major component of the natural product was determined as L, the chirality of the a-methyl group of the isopalmitic acid part was unambiguously assigned as R. This has been confirmed by co-injection of the natural pheromone and the synthesized compound.

Formula I. Chemical structure of the natural host marking pheromone (HMP) of *Anastrepha ludens* indicating carbon numbering.

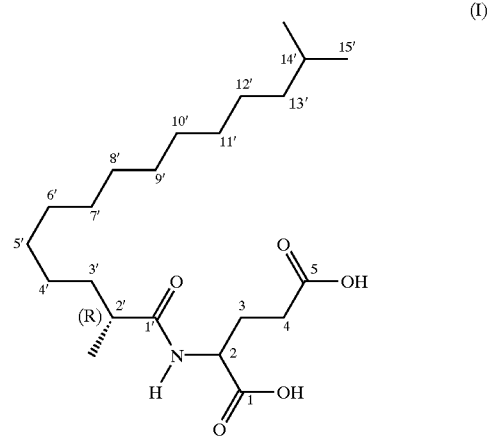

(I)

Where the stereochemistry at C-2 is 79:21 (L):(D)

I. Synthesis of Compounds of the Formula II

The process according to the invention for the preparation of compounds of the formula (II) is carried out analogously to known literature procedures and involves either a) reaction of a compound of the formula (III)

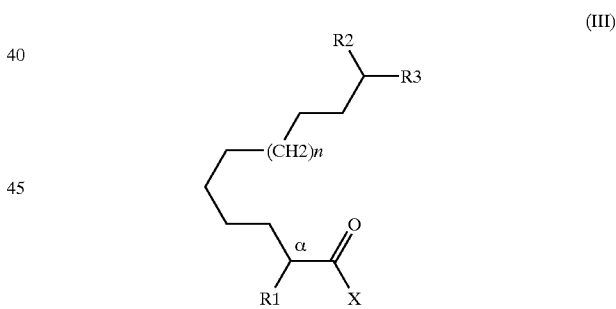

(III)

where R1, R2, R3, n and α are as defined under formula (II), where X is an acid activating group, for example halogen, in an inert organic solvent in the presence of a base, with a compound of the formula (IV)

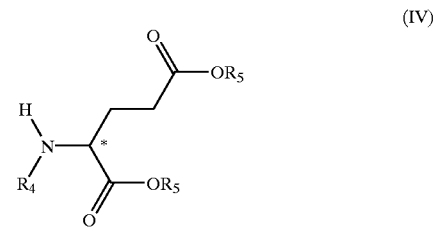

(IV)

in which R4 and * are as defined in formula (II), and where R5 represent cleavable protecting groups, to give the compounds of the formula (V)

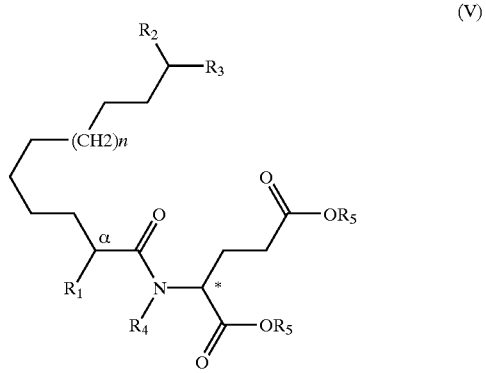

(V)

in which the protecting groups R5 of these compounds are cleaved and replaced by H, or b) reaction of a compound of the formula (III)

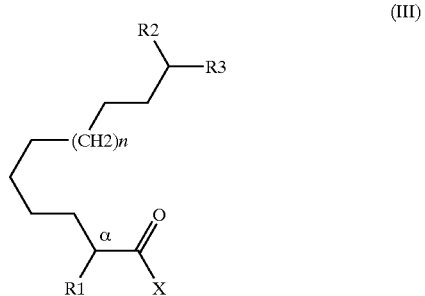

(III)

where R1, R2, R3, n and α are as defined under formula (II), and X is an acid activating group, for example halogen, in an inert organic solvent in the presence of a base, and a solubilizing agent, for example lithium chloride, with a compound of the formula (VI)

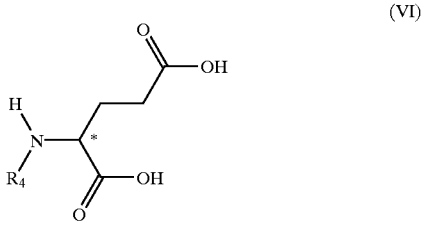

(VI)

in which R4 and * are as previously defined.

Compounds of the formula (VI) are glutamic acid derivatives and are widely available. Compounds of the formula (IV) contain protecting groups R5 which are typical protecting groups used in peptide, chemistry. Examples of such are C1–C4 alkyl; benzyl which is substituted once to three times on the phenyl ring by halogen, C1–C4 alkyl; C3–C4 alkenyl.

The alkyl, alkenyl and alkynyl groups in the above definitions can be straight chain or branched. Alkyl groups for example are methyl, ethyl, n-propyl, isopropyl, n-butyl, sec-butyl, iso-butyl, and tert-butyl. As an example of an alkenyl protecting group, allyl is preferred.

Especially preferred are compounds where R5 is benzyl.

The protecting groups can be introduced and removed by known methods (see for example Greene, 1981). For example a compound of the formula (V) where R5 is benzyl, deprotection can be achieved by standard catalytic hydrogenation, or by catalytic hydrogen transfer hydrogenation as described in the literature (Means et al., 1979).

The activating groups X used for the coupling of compound (III) with compounds (IV) and (VI) are, for example halogen, or activated esters well known in peptide synthesis (see for example Geiger, 1985). Preferred methods for activation of the acid (compound (III), X=OH) are formation of the acid chloride, using for example thionyl chloride with a catalytic amount of dimethylformamide, or formation of the activated esters using, for example, N-ethyl-N'-(3-dimethylaminopropyl)-carbodimide (EDC) or dicyclohexylcarbodiimide. The reaction of compound (III) with compound (IV) is carried out in an inert organic solvent, for example, a chlorinated hydrocarbon solvent such as dichloromethane, or an aromatic hydrocarbon solvent, such as toluene, in the presence of a base, for example an alkyl amine such as triethylamine or an aromatic amine, for example 4-dimethylaminopyridine (DMAP), or a combination of bases. The reaction can be carried out at temperatures between 0 and 120° C. Reaction of compounds of the formula (VI) with compounds of the formula (III) are carried out in the presence of a solubilizing agent such as LiY, where Y is a halogen, for example chloride, in an inert ether solvent, such as tetrahydrofuran, at temperatures between 0 and 120° C. The use of solubilizing agents in peptide chemistry is well known in the literature (Seebach et al., 1995).

Compounds of the formula (III) containing an α substituent group can be prepared in racemic form according to literature methods (see for example Hoefle et al., U.S. Pat. No. 4,716,175 A, 1987). The compounds of formula (V) are subsequently formed as mixtures of diastereoisomers and may be separated by, for example HPLC methodology.

Alternatively compounds of formula (III) (where R1 is not H) may be prepared in a stereospecific manner by attaching a group containing at least one chiral center (a chiral auxiliary) to a compound of formula (III) (where R1 is H), which leads to a chiral compound of formula (VII), which can then be reacted with a compound R1-Y, where R1 is as previously defined, with the premise that it is not H, and Y is halogen, to give a compound of formula (VIII), and then removal of the chiral auxiliary, to give compounds of the formula (III). Subsequent activation and reaction of these compounds with compounds of the formula (IV) or (VI) leads to compounds of the formula (II) or (V), where R1 is not H, in non-racemic form, as illustrated in Scheme 1.

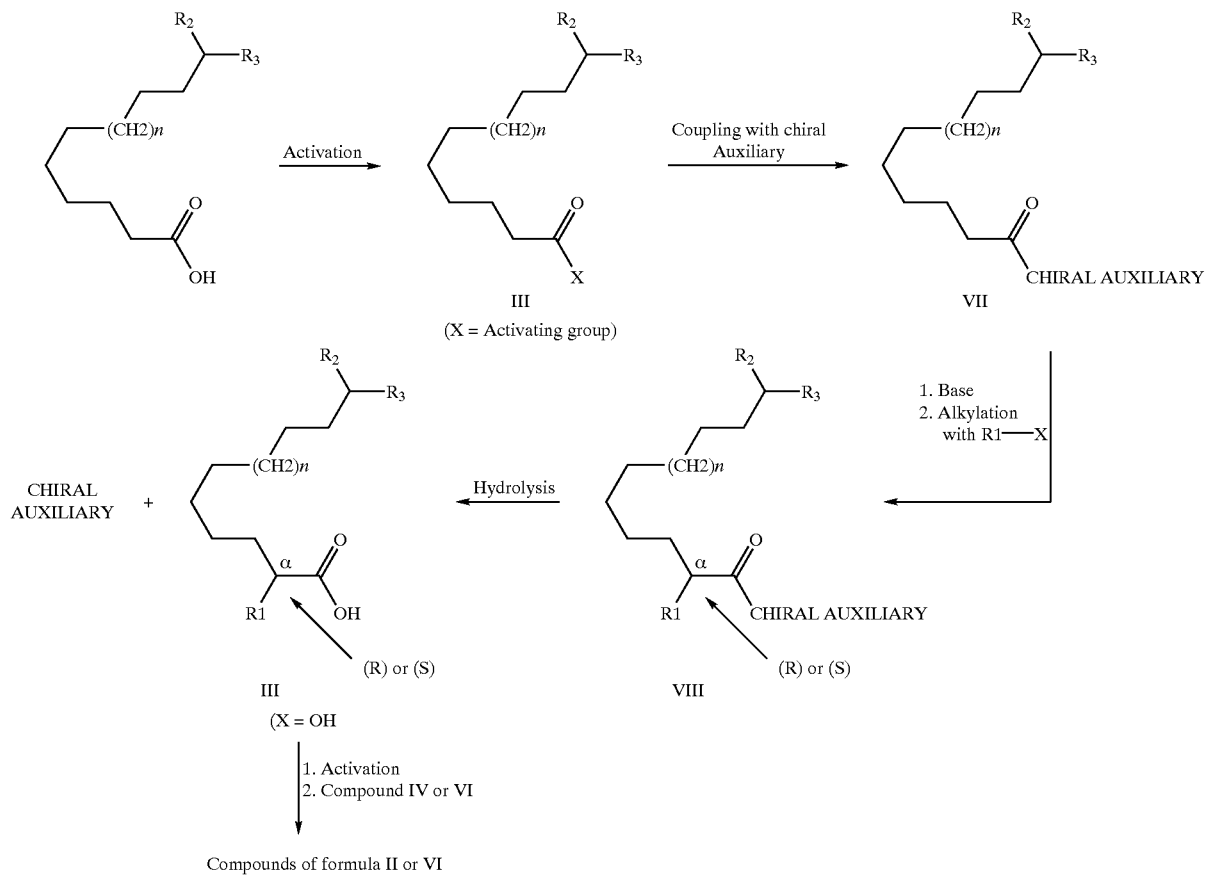

The use of chiral auxiliaries in stereospecific synthesis is well known (Ager et al., 1995). Chiral auxiliaries are, for example, 2-(R)- or 2-(S)-Bornane-10,2-sultams,

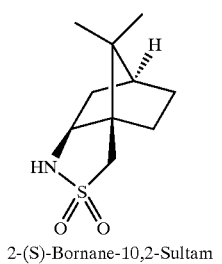
2-(S)-Bornane-10,2-Sultam

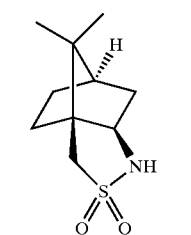
2-(R)-Bornane-10,2-Sultam which can be coupled to compounds of formula (IIIa), where X is an activating group for example chlorine, and where R2, R3 and n are as defined in formula (II), and R1 is H, to give compounds of the formula (VIIa) and (VIIb).

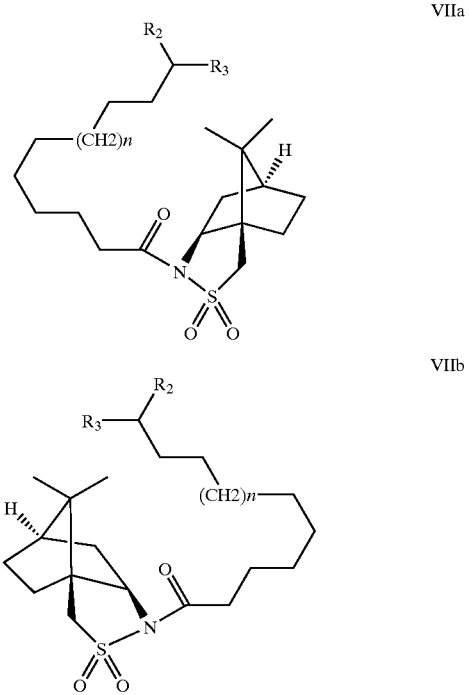

Compounds of formula (VIIa) can be deprotonated with a strong base, for example n-butyl lithium, in an inert solvent, such as tetrahydrofuran, and a dipolar aprotic co-solvent, such as 1,3-dimethyl-tetrahydro-2-(1H)-pyrimidone (DMPU), and subsequently reacted with.an alkylating agent R1-Y, where R1 is as previously defined, with the premise that it is not H, and Y is halogen, for example iodide, to give a compound (VIIIa), preferentially of the R1-α-configuration illustrated for (VIIIa).

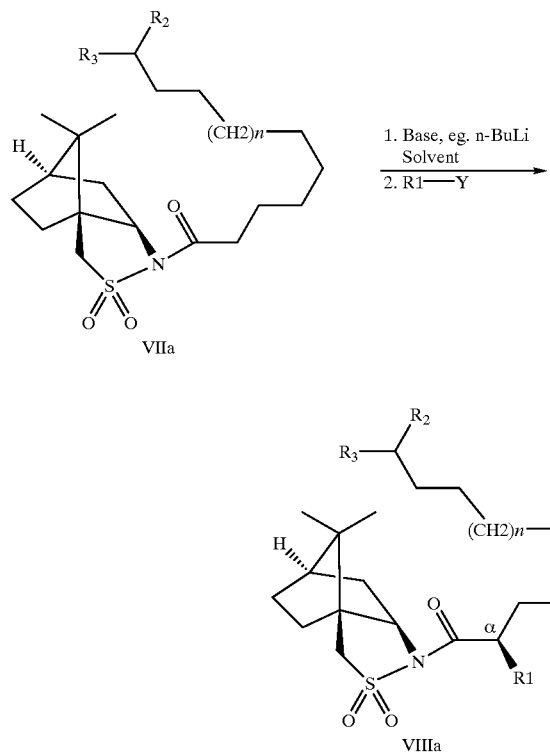

Analogously, compounds of formula (VIIb) can be reacted with compounds R1-Y to give compounds of type (VIIIb), where the R1-α-configuration is predominantly as shown in (VIIIb).

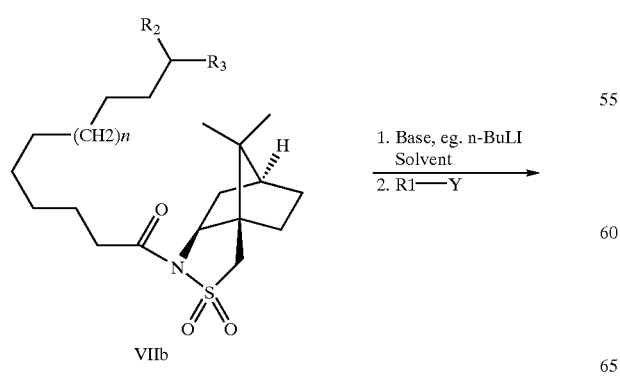

-continued

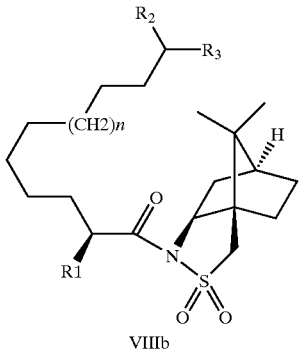

VIIIb

Face selective alkylations of this type are predictable and well documented in the literature (Oppolzer et al., 1989).

The chiral auxiliaries can be removed from compounds of the formula (VIII) by, for example, hydrolysis by a base, for example lithium hydroxide, in an inert solvent, such as tetrahydrofuran, and an a protic solvent, such as water, in the presence of a inorganic peroxide, such as hydrogen peroxide, analogously to literature procedures (Evans et al., 1987). After activation, compounds of formula (III), where X is an activating group, for example chlorine, can be used to prepare compounds of the formula (II) with defined α-stereochemistry, based upon the mechanistic discussions of Opollzer et al., (1989).

One skilled in the art will realize that compounds of the formula (II) can be prepared according to this process with defined stereochemistry at the α and * positions by judicious choice of the chiral auxiliary, and the L- or D-isomers of compounds of formula (IV) or (VI).

The following examples (1–36) illustrate the stereospecific synthesis of the invention without limiting it:

Compounds of the Formula VIIa and VIIb

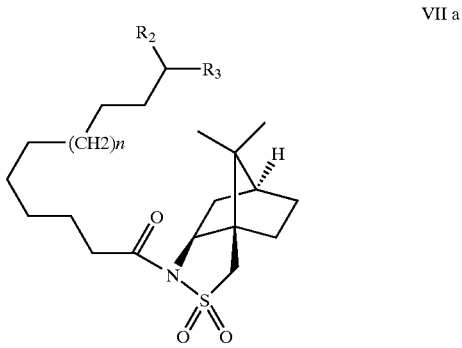

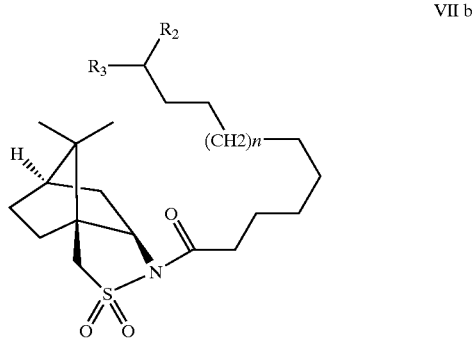

EXAMPLE 1

(Compound VIIb1, $R_2$=Me, $R_3$=Me, n=5):

A solution of 750 mg of 14-methyl-pentadecanoic acid (prepared as described by C. Djerassi et al., J. Org. Chem., 51:2751, 1986) in thionyl chloride (10 ml) was stirred at room temperature and treated with one or two drops of dimethyl formamide. The solution was stirred at room temperature until gas evolution ceased (ca. 1 hr.). The excess thionyl chloride was removed in vacuo and the residue then dissolved in anhydrous toluene (10 ml). This solution was then added at room temperature to a suspension of 2-(R)-Bornane-10,2-sultam sodium salt (which had been prepared by treating 2-(R)-Bornane-10,2-sultam sultam (692 mg) dissolved in anhydrous toluene (40 ml) with sodium hydride (200 mg of 80% sodium hydride in mineral oil) at room temperature). The reaction mixture was stirred at room temperature until TLC analysis (5:1 hexane: ethyl acetate) showed reaction completion (ca. 1 hr.). The reaction mixture was then diluted with ethyl acetate and 10% aqueous HCl, the organic layer decanted, washed with $NaHCO_3$ (10% in water), and then dried over $Na_2SO_4$ and concentrated in vacuo. The crude compound was purified by flash chromatography to give of (VIIb1) (1.208 g) as a pale oil.

(Compound VIIb1, $R_2$=Me, $R_3$=Me, n=5):

Selected $^1$H NMR Data (in $CDCl_3$ in ppm) 0.854, 6H, d, (J=5.7 Hz); 0.963, 3H, s; 1.114, 2H, m; 1.51, 3H, s; 1.240, br. s; 2.69, 2H, m; 3.38–3.51, 2H, AB quartet (J=22.3 Hz and 14.1 Hz); 3.36, 1H, t, (J=6.1 Hz).

The following compounds were prepared in an analogous fashion:

EXAMPLE 2

(Compound VIIb2, $R_2$=Me, $R_3$=H, n=5):

Selected $^1$H NMR data (in $CDCl_3$ in ppm): 0.873, 3H, t, (J=6.4 Hz); 0.963, 3H, s; 1.150, 3H, s; 1.240, br. s; 2.69, 2H, m; 3.38–3.51, 2H, AB quartet (J=22 Hz and 14.3 Hz); 3.37, 1H, t, (J=6.0 Hz).

EXAMPLE 3

(Compound VIIa1, $R_2$=Me, $R_3$=Me, n=5):

Enantiomer of example 1, identical NMR.

EXAMPLE 4

(Compound VIIa2, $R_2$=Me, $R_2$=H, n=5):

Enantiomer of example 2, identical NMR.

Compounds VIIIa and VIIIb

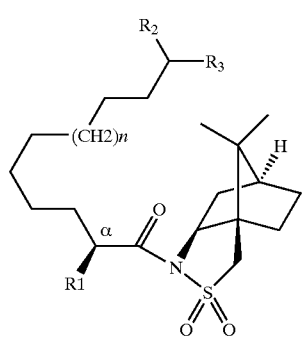

VIIIa

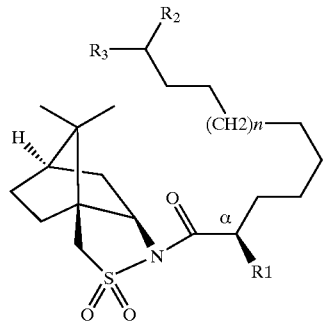

VIIIb

EXAMPLE 5

(Compound VIIIb1, $R_1$=$R_2$=R3=Me, $\alpha$=(R) Stereochemistry, n=5):

A solution of 1.1 g of (VIIb1) in tetrahydrofurane (15 ml) was cooled to –78° C. under nitrogen and then treated dropwise over 10 min with a solution of n-butyl lithium (1.6 M in hexane, 1.6 ml.). This solution was stirred at –78° C. and then treated with DMPU (3.83 ml) over 15 min. The solution was allowed to stir for 1 hr at –78° C. and then treated with methyl iodide (5 eq.) at this temperature. The reaction was monitored by TLC (9:1 hexane: ethyl acetate) until reaction completion (ca. 4–6 hr). The reaction mixture was treated at –78° C. with 10% HCl and ethyl acetate and then allowed to warm to room temperature. The organic phase was decanted, t he aqueous phase back extracted with ethyl acetate and the combined organic phases washed with water, and then with 10% aqueous $NaHCO_3$. Drying over $Na_2SO_4$ and concentration in vacuo gave the crude product as an oil. $^1$H-NMR analysis of the crude product (NMR integration of triplets at 3.893 ppm (J=6.3 Hz, major isomer) and 3.667 ppm (J=6.3 Hz, minor isomer)) showed the diastereoselectivity of the alkylation to be ca. 9:1. The diastereoisomers could be separated by chromatography and/or recrystallization. The yield of the main isomer compound (VIIIb1) (R1=$R_2$=$R_3$=Me, $\alpha$=(R) Stereochemistry, n=5) was 782 mg (white crystals).

mpt: 39.4–39.5° C.

Compound VIIIb1

Selected $^1$H-NMR data ($CDCl_3$ in ppm): 0.854, 6H, d, (J=6.6 Hz); 0.963, 3H, s; 1.114, 2H, m; 1.51 , 3H, s; 1.19, 3H, d, (J=6.9 Hz); 1.235, br. s; 3.04, 1H, m; 3.39–3.52, 2H, AB quartet (J=24 Hz and 12 Hz); 3.893, 1H, t, (J=6.3 Hz).

$^{13}$C-NMR (n $CDCl_3$): 18.895; 19.734; 20.681; 22.534; 26.318; 27.171; 27.293; 27.831; 29.539; 29.488; 29.538; 29.567; 29.602; 29.818; 32.567; 32.686; 38.352; 38.947; 40.246; 44.513; 47.611; 48.135; 53.091; 64.996; 176.455.

The following compounds were prepared analogously:

EXAMPLE 6

(Compound VIIIb2, R1=Me, $R_2$=H, $R_3$=Me, $\alpha$=(R) Stereochemistry, n=5): Diastereoselectivity >98:2 (NMR integration of triplets at 3.893 (major isomer) and 3.730 ppm (minor isomer): Purification by flash chromatography and recrystallization (–20° C. pentane) mpt 39.5–40.6° C.

Selected $^1$H-NMR data (in $CDCl_3$ in ppm): 0.875, 3H, t, (J=6.9 Hz); 0.951, 3H, s; 1.139, s; 1.195, 3H, d, (J=6.6 Hz); 3.041, 1H, m; 3.400–3.521, 2H, AB quartet (J=22.5 Hz and 13.8 Hz); 3.893, 1H, t (J=6.2 Hz).

EXAMPLE 7

(Compound VIIIa1, R1=$R_2$=$R_3$=Me, $\alpha$=(S) Stereochemistry, n=5): Diastereoselectivity >98:2 (minor isomer not detected). Purification by flash chromatography and recrystallization (pentane −20° C., mpt=40.1–40.8° C.). $^1$H-NMR: As for example 5 (enantiomers).

EXAMPLE 8

(Compound VIIIa2, R1=Me, R$_2$=H, R$_3$=Me, α=(S) Stereochemistry, n=5): Diastereoselectivity 97:3 (NMR integration of triplets at 3.893 (major isomer) and 3.667 ppm (minor isomer).

Purification by flash chromatography and recrystallization (−20° C., pentane, mpt: 39.5–39.6° C.).

$^1$H-NMR: As for example 6 (enantiomers).

Compound III

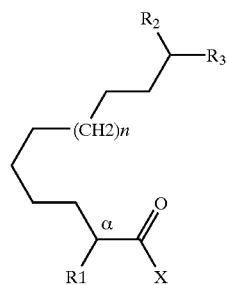

EXAMPLE 9

(Compound III1, X=OH, R1=R$_2$=R$_3$=Me, α=(R) Stereochemistry, n=5):

A solution of compound (VIIIb1) (750 mg) in tetrahydrofuran: H$_2$O 4:1 (50 ml) was cooled to 0° C. and then treated with LiOH.H$_2$O (264 mg) and 30% aqueous H$_2$O$_2$ (714 mg). The suspension was stirred at 0° C. for 1 hr and then allowed to warm to room temperature and stirred at this temperature until reaction completion (TLC analysis, 3:1 hexane: ethyl acetate, 6–18 hr.). The reaction mixture was then treated with 10% aqueous NaHSO$_3$, acidified with 10% aqueous HCl, and extracted with ethyl acetate. The ethyl acetate phase was washed with H$_2$O, dried over Na$_2$SO$_4$ and concentrated in vacuo. The crude product residue was triturated in pentane, the white crystals of 2-(R)-bornane-10,2-sultam filtered at the pump, and the filtrate concentrated in vacuo to give the acid (III1) which could be used in the next step without further purification. An analytical sample could be obtained by recrystallization from pentane at −20° C.

(Compound III1, X=OH, R1=R$_2$=R$_3$=Me, α=(R) Stereochemistry, n=5):

mpt: 25.7–26.4° C. $^1$H-NMR (CDCl$_3$ in ppm): 0.856, 6H, d, (J=6.9 Hz); 1.114, 2H, m; 1.172, 3H, d, (J=7.2 Hz); 1.249, br. s; 1.42, 1H, m; 1.51, 1H, m; 1.66, 1H, m; 2.45, 1H, m.

The following compounds were prepared analogously:

EXAMPLE 10

(Compound III2, X=OH, R1=Me, R$_2$=H, R$_3$=Me, α=(R) Stereochemistry, n=5):

mpt: 39.0–40.6° C. $^1$H-NMR (CDCl$_3$ in ppm): 0.875, 3H, t, (J=7.2 Hz); 1.171, 3H, d, (J=6.9 Hz); 1.249, br. s; 1.42, 1H, m; 1.66, 1H, m; 2.45, 1H, m.

EXAMPLE 11

(Compound III3, X=OH, R1=R$_2$=R$_3$=Me, α=(S) Stereochemistry, n=5):

mpt: 25.4–26.5° C. $^1$H-NMR: As for example 9 (enantiomers).

EXAMPLE 12

(Compound III4, X=OH, R1=Me, R$_2$=H, R$_3$=Me, α=(S) Stereochemistry, n=5):

mpt: 39.5–39.6° C. $^1$H-NMR: As for example 10 (enantiomers)

Compound V

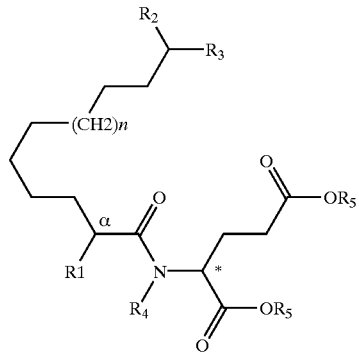

EXAMPLE 13

(Compound V1, R$_1$=Me, R$_2$=Me, R$_3$=Me, R4=H, R5=Benzyl, α=(R) Stereochemistry, *=(L) Stereochemistry, n=5):

A sample of acid (III1) (6.77 g) in methylene chloride (300 ml) was treated at room temperature sequentially with 13.86 g of (L)-H-Glu(OBn-OBn).para-toluene-sulphonate, triethylamine (5.6 g) and cooled to 0° C. This solution was then treated with N-ethyl-N'-(3-dimethylaminopropyl)-carbodimide (5.3 g) and allowed to warm to room temperature and the reaction mixture stirred at this temperature until TLC analysis (5:1 hexane: ethyl acetate) showed reaction completion (4–6 hr.). The reaction mixture was diluted with methylene chloride and then washed successively with 10% aqueous HCl, H$_2$O, and then saturated aqueous NaHCO$_3$. Drying over Na$_2$SO$_4$ and concentration in vacuo gave the crude product which was purified by flash chromatography (8:1 hexane: ethyl acetate) to give 9.1 g of the title compound as white crystals.

(Compound V1, R$_1$=Me, R$_2$=Me, R$_3$=Me, R4=H, R5=Benzyl, α=(R) Stereochemistry, *=(L) Stereochemistry, n=5):

mpt: 74.2–76.4° C. $^1$H-NMR (CDCl$_3$ in ppm): 0.873, 6H, d, (J=6.6 Hz); 1.122, 3H, d, (J=6.9 Hz); 1.145, 2H, m; 1.238, br. s; 1.26–1.68, 3H, m; 2.02, 1H, m; 2.12–2.52, 4H, m; 4.68, 1H, m; 5.11, 2H, s; 5.18, 2H, s; 6.14, 1H, br. d, (J=7.6 Hz); 7.38, 10H, br. s. $^{13}$C-NMR (CDCl$_3$ in ppm) 17.955; 22.53; 27.99; 27.328; 27.837; 29.487; 29.530; 29.588; 29.608; 29.824; 30.146; 34.115; 38.946; 41.299; 51.425; 66.465; 67.240; 128.15; 128.287; 128.316; 128.502; 128.581; 128.638; 135.255; 135.855; 172.955; 172.855; 177.855.

The following compounds were prepared analogously:

EXAMPLE 14

(Compound V2, R$_1$=Me, R$_2$Me, R$_3$=Me, R4=H, R5=Benzyl, α=® Stereochemistry, *=(D) Stereochemistry, n=5):

mpt: 64.6–64.7° C. $^1$H-NMR (CDCl$_3$ in ppm): 0.861, 6H, d, (J=6.6 Hz); 1.122, 3H, d, (J=6.9 Hz); 1.105, 2H, m; 1.241, br. S; 1.26–1.68, 3H, m; 2.02, 1H, m; 2.12–2.52, 4H, m; 4.68, 1H, m; 5.097, 2H, s; 5.160, 2H, s; 6.18, 1H, br. D, (J=7.6 Hz); 7.38, 10H, br. S. $^3$C-NMR (CDCl$_3$ in ppm): 17.566; 22.544; 27.069; 27.2 27; 27.306; 27.851; 29.393; 29.508; 29.522; 29.551; 29.579; 29.602; 29.838; 30.168; 34.062; 38.960; 41.262; 51.418; 66.493; 67.232; 128.272; 128.287; 128.351; 128.469; 128.609; 128.652; 135.222; 135.702; 171.935; 172.846; 176.805.

EXAMPLE 15

(Compound V3, R$_1$=Me, R$_2$=Me, R$_3$=Me, R4=H, R5=Benzyl, α=(S) Stereochemistry, *=(L) Stereochemistry, n=5):

mpt: 64.5–64.9° C. Spectral data identical to example 14 (enantiomers).

EXAMPLE 16
(Compound V4, $R_1$=Me, $R_2$=Me, $R_3$=Me, R4=H, R5=Benzyl, α=(S) Stereochemistry, *=(D) Stereochemistry, n=5):
mpt: 74.6–75.4° C. Spectral data identical to example 13 (enantiomers).

EXAMPLE 17
(Compound V5, $R_1$=Me, $R_2$=H, $R_3$=Me, R4=H, R5=Benzyl, α=®  Stereochemistry, *=(L) Stereochemistry, n=5):
mpt: 79.2–79.8° C. $^1$H-NMR (CDCl$_3$ in ppm): 0.809, 3H, t, (J=6.9 Hz); 1.0385, 3H, d, (J=6.9 Hz); 1.166 br. S; 1.28, 1H, m; 1.54, 1H m; 1.966, 1H, m; 2.093–2.449, 4H, m; 4.603, 1H, m; 5.026, 2H, s; 5.088, 2H, s; 6.078, 1H, br. D, (J=7.2 Hz); 7.38, 10H, br. S. $^{13}$C-NMR (in ppm in CD$_3$OD: CDCl$_3$, 9:1): 14.417; 18.326; 23.647; 27.319; 28.581; 30.403; 30.539; 30.632; 30.697; 30.712; 30.726; 31.185; 32.992; 35.194; 41.706; 52.757; 67.409; 67.897; 137.06; 137.112; 173.042; 174.046; 180.013.

EXAMPLE 18
(Compound V6, $R_1$=Me, $R_2$=H, $R_3$=Me, R4=H, R5=Benzyl, α=(R) Stereochemistry, *=(D) Stereochemistry, n=5):
mpt: 64.5–65.1° C. $^1$H-NMR (CDCl$_3$ in ppm): 0.809, 3H, t, (J=6.9 Hz); 1.0384, 3H, d, (J=6.9 Hz); 1.167 br. S; 1.28, 1H, m; 1.54, 1H m; 1.966, 1H, m; 2.093–2.449, 4H, m; 4.603, 1H, m; 5.026, 2H, s; 5.09, 2H, s; 6.078, 1H, br. D, (J=7.2 Hz); 7.38, 10H, br. S. $^{13}$C-NMR (in CD$_3$OD: CHCl$_3$ 9:1 in ppm): Identical to example 17 with the exception of the following peaks: 28.388; 35.015; 52.872; 173.035; 174.117; 180.070.

EXAMPLE 19
(Compound V7, $R_1$=Me, $R_2$=H, $R_3$=Me, R4=H, R5=Benzyl, α=(S) Stereochemistry, *=(L) Stereochemistry, n=5):
mpt: 62.2–62.7° C. Spectral data identical to example 18 (enantiomers).

EXAMPLE 20
(Compound V8, $R_1$=Me, $R_2$=H, $R_3$=Me, R4=H, R5=Benzyl, α=(S) Stereochemistry, *=(D) Stereochemistry, n=5):
mpt: 78.3–79.4° C. Spectral data identical to example 17 (enantiomers).

EXAMPLE 21
(Compound V9, $R_1$=H, $R_2$=Me, $R_3$=Me, R4=H, R5=Benzyl, *=(L) Stereochemistry, n=5):
mpt: 62.2–62.7° C. $^1$H-NMR (CDCl$_3$ in ppm): 0.867, 6H, d, (J=6.6 Hz); 1.145, 2H, m; 1.243, br s; 1.44–1.66, 3H, m; 2.603, 1H, m; 2.160, 2H, t, (J=7.9 Hz); 2.160–2.51, 2H, m; 4.68, 1H, m; 5.11, 2H, s; 5.18, 2H, s: 6.17, 1H, br d, (J=7.2 Hz); 7.38, 10H, br s. $^{13}$C-NMR (in CDCl$_3$ in ppm): 22.48; 22.509; 25.371; 27.085; 27.264; 27.809; 29.100; 29.186; 29.322; 29.473; 29.509; 29.538; 29.573; 29.796; 30.119; 36.315; 38.918; 51.469; 66.416; 67.190; 128.216; 128.223; 128.230; 128.252; 128.295; 128.467; 128.539; 128.560; 128.567; 135.173; 135.682; 171.929; 172.732; 173.241.

EXAMPLE 22
(Compound V10, $R_1$=H, $R_2$=Me, $R_3$=Me, R4=H, R5=Benzyl, *=(D) Stereochemistry, n=5):
mpt: 62.3–63.4° C. Spectral data identical to Example 21 (enantiomers).

EXAMPLE 23
(Compound V11, $R_1$=H, $R_2$=H, $R_3$=Me, R4=H, R5=Benzyl, *=(L) Stereochemistry, n=5):
mpt: 45.5–46.0° C. $^1$H-NMR (CDCl$_3$ in ppm): 0.867, 3H, t, (J=6.9 Hz); 1.243, br. s; 1.48–1.66, 2H, m; 2.603, 1H, m; 2.160, 2H, t, (J=7.9 Hz); 2.160–2.51, 2H, m; 4.68, 1H, m; 5.11, 2H, s; 5.18, 2H, s; 6.17, 1H, br. d, (J=7.4 Hz); 7.38, 10H, br. s.

EXAMPLE 24
(Compound V12, $R_1$=H, $R_2$=H, $R_3$=Me, R4=H, R5=Benzyl, *=(D) Stereochemistry, n=5):
mpt: 47.0–48.10° C. Spectral data identical to example 23 (enantiomers).

Compound IIa (IIa)

EXAMPLE 25
(Compound IIa1, $R_1$=Me, $R_2$=Me, $R_3$=Me, α=(R) Stereochemistry, *=(L) Stereochemistry, n=5):
A solution of (V1) (6.45 g) in MeOH: ethyl acetate (1:1, 500 ml) was stirred at room temperature and treated with 10% Pd on charcoal (150 mg) under an atmosphere of hydrogen. After 24 hr., the reaction was shown to be complete. The solution was filtered over Hyflo Super Cel®, which was washed with ethyl acetate and concentrated in vacuo, to give the crude product which was titrated with hexane. This gave the title compound (V1) (3.44 g) as a white powder. This was analyzed by NMR and HPLC (HPLC conditions: Col.: Nucleosil RP Phenyl 10×250 mm: Eluent: 60% H$_2$O: 40% CH$_3$CN with 0.1% formic acid: Flow: 4 ml/min.: Detection: Diode, 195 nm.)
(Compound IIa1, $R_1$=Me, $R_2$=Me, $R_3$=Me, α=(R) Stereochemistry, *=(L) Stereochemistry, n=5):
mpt: 84–85° C. $^1$H-NMR (CD$_3$OD in ppm): 0.880, 6H, d, (J=6.6 Hz); 1.108, 3H, d, (J=6.6 Hz); 1.91, 2H, m; 1.286, br. s; 1.32, 1H, m; 1.54, 1H, m; 1.61, 1H, m; 1.953, 1H, m; 2.180, 1H, m; 2.394, 2H, t, (J=7.5 Hz); 2.31–2.42, 1H, m; 4.413, 1H, m; 8.13, 1H, br. d, (J=7.4 Hz) $^{13}$C-NMR (CD$_3$OD in ppm): 18.170; 23.001; 28.503; 28.608; 29.110; 30.639; 30.696; 30.736; 30.785; 31.012; 35.389; 40.228; 42.000; 53.800; 177.300 (br. 2C); 179.7. HPLC: Ret. Time: 46.0 min The following compounds were prepared analogously:

EXAMPLE 26
(Compound IIa2, $R_1$=Me, $R_2$=Me, $R_3$=Me, α=(S) Stereochemistry, *=(L) Stereochemistry, n=5):
$^1$H-NMR (CD$_3$OD in ppm): 0.880, 6H, d, (J=6.6 Hz); 1.108, 3H, d, (J=6.6 Hz); 1.91, 2H, m; 1.286, br. s; 1.32, 1H, m; 1.54, 1H, m; 1.61, 1H, m; 1.953, 1H, m; 2.180, 1H, m; 2.394, 2H, t, (J=7.5 Hz); 2.31–2.42, 1H, m; 4.413, 1H, m; 8.13, 1H, br. d, (J=7.4 Hz). $^{13}$C-NMR (CD$_3$OD in ppm): 18.364; 23.008; 27.823; 28.422; 28.503; 30.639; 30.704; 30.744; 30.793; 31.011; 35.270; 40.228; 41.838; 52.940; 175.306; 176.68; 180.09. HPLC: Ret. Time: 48.0 min.

EXAMPLE 27

(Compound IIa3, $R_1$=Me, $R_2$=Me, $R_3$=Me, $\alpha$=(S) Stereochemistry, *=(D) Stereochemistry, n=5):

NMR identical to example 25 (enantiomers). HPLC: Ret. Time: 46.0 min.

EXAMPLE 28

(Compound IIa4, $R_1$=Me, $R_2$=Me, $R_3$=Me, $\alpha$=(R) Stereochemistry, *=(D) Stereochemistry, n=5):

NMR identical to example 26 (enantiomers). HPLC: Ret. Time: 48.0 min.

EXAMPLE 29

(Compound IIa5, $R_1$=Me, $R_2$=H, $R_3$=Me, $\alpha$=(R) Stereochemistry, *=(L) Stereochemistry, n=5):

mpt: 94–95° C. $^1$H-NMR (CD$_3$OD in ppm): 0.897, 3H, t, (J=7.2 Hz); 1.103 3H, d, (J=6.6 Hz); 1.286, br. s; 1.32, 1H, m; 1.61, 1H, m; 1.953, 1H, m; 2.180, 1H, m; 2.394, 2H, t, (J=7.5 Hz); 2.31–2.42, 1H, m; 4.413, 1H, m; 8.13, 1H, br. d, (J=7.4 Hz). $^{13}$C-NMR (CD$_3$OD in ppm): 14.435; 18.212; 23.670; 28.037; 28.597; 30.447; 30.648; 30.705; 30.734; 30.748; 30.777; 31.445; 33.036; 41.893; 52.786; 176.870 (br. 2C); 179.775. HPLC: Ret. Time: 36.8 min.

EXAMPLE 30

(Compound IIa6, $R_1$=Me, $R_2$=H, $R_3$=Me, $\alpha$=(R) Stereochemistry, *=(D) Stereochemistry, n=5):

$^1$H-NMR (CD$_3$OD in ppm): 0.897, 3H, t, (J=7.2 Hz); 1.103 3H, d, (J=6.6 Hz); 1.286, br. s; 1.32, 1H, m; 1.61, 1H, m; 1.953, 1H, m; 2.180, 1H, m; 2.394, 2H, t, (J=7.5 Hz); 2.31–2.42, 1H, m; 4.413, 1H, m; 8.13, 1H, br. d, (J=7.4 Hz). $^{13}$C-NMR (CD$_3$OD in ppm): 14.435; 18.319; 23.670; 28.037; 28.417; 30.447; 30.648; 30.705; 30.734; 30.748; 30.777; 31.955; 33.036; 41.893; 52.044; 176.870 (br. 2C); 179.775. HPLC: Ret. Time: 38.5 min.

EXAMPLE 31

(Compound IIa7, $R_1$=Me, $R_2$=H, $R_3$=Me, $\alpha$=(S) Stereochemistry, *=(D) Stereochemistry, n=5):

NMR identical to example 29 (enantiomers). HPLC: Ret. Time: 36.8 min.

EXAMPLE 32

(Compound IIa8, $R_1$=Me, $R_2$=H, $R_3$=Me, $\alpha$=(S) Stereochemistry, *=(L) Stereochemistry, n=5):

NMR identical to example 30 (enantiomers). HPLC: Ret. Time: 38.2 min.

EXAMPLE 33

(Compound IIa9, $R_1$=H, $R_2$=$R_3$=Me, *=(L) Stereochemistry, n=5): $^1$H-NMR (CD$_3$OD in ppm): 0.885, 6H, d, (J=6.6 Hz); 1.189, 2H, m; 1.286, br. s; 1.521, 1H, m; 1.61, 1H, m; 1.93, 1H, m; 2.160, 1H, m; 2.240, 2H, t, (J=7.7 Hz); 2.39, 2H, t, (J=7.7 Hz); 4.42, 1H, m; 8.13, 1H, br. d, (J=7.4 Hz).

EXAMPLE 34

(Compound IIa10, $R_1$=H, $R_2$=$R_3$=Me, *=(L) Stereochemistry, n=5):

NMR identical to example 33 (enantiomers).

EXAMPLE 35

(Compound IIa11, $R_1$=$R_2$=H, $R_3$=Me, *=(L) Stereochemistry, n=5): $^1$H-NMR (CD$_3$OD in ppm): 0.899, 3H, t, (J=6.4 Hz); 1.282, br. s; 1.61, 2H, m; 1.94, 1H, m; 2.18, 1H, m: 2.240, 2H, t, (J=7.7 Hz); 2.39, 2H, t, (J=7.7 Hz); 4.42, 1H, m; 8.12, 1H, br. d, (J=7.4 Hz).

EXAMPLE 36

(Compound IIa12, $R_1$=$R_2$=H, $R_3$=Me, *=(D) Stereochemistry, n=5):

NMR identical to example 35 (enantiomers).

The following illustrates the non stereospecific synthesis of the invention (example 37), and the resultant separation of the mixture into the pure diastereoisomers (examples 38 and 39).

EXAMPLE 37

(Compound IIa13, $R_1$=Me, $R_2$=H, $R_3$=Me, $\alpha$=(R/S) Stereochemistry, *=(L) Stereochemistry, n=6):

A suspension of (L)-glutamic acid in 60 ml of tetrahydrofuran was treated with anhydrous LiCl (600 mg) and then 2 g of racemic 2-methylhexadecanoyl chloride (prepared according to Hoefle et al., 1987), dissolved in 40 ml of tetrahydrofuran at room temperature. After stirring for 6 hr, the solvent was removed in vacuo and the remaining gum titrated with hexane (4×200 ml), to give the compound (IIa13) (1.2 g) as a white powder.

(Compound IIa13, $R_1$=Me, $R_2$=H, $R_3$=Me, $\alpha$=(R/S) Stereochemistry, *=(L) Stereochemistry, n=6):

mpt: 133.0–135.0° C. HPLC: Ret. Time: 52.6 (R) and 55.6 (S) min. (1:1 Ratio).

Resolved diastereomeric counterparts are connected with "and".

$^1$H-NMR (in CD$_3$OD [=3.30 ppm], 50 mg/ml, 300 MHz, Room temp.): 4.44 and 4.42 (each dd, J=8.4, 4.8, 1H), 2.40 (m, 3H), 2.17 (br. m, 1H), 1.94 (br. m, 1H), 1.60 (m, 1H), 1.29 (br., 25H), 1.10 (d, J=6.9, 3H), 0.89 (t, J=6.6, 3H). $^{13}$C-NMR (in CD$_3$OD [=49.0 ppm], 50 mg/ml, 75 MHz, Room temp.):. 180.11 and 180.05, 176.59 and 176.51, 175.24 and 175.17, 52.82 and 52.78, 41.86 and 41.83, 35.39 and 35.28, 33.04, 31.26 and 31.23, 30.74 (5C), 30.69 (2C), 30.63, 30.43, 28.60 and 28.41, 27.75 and 27.71, 23.67, 18.34 and 18.22, 14.38.

The diastereomers for examples 38 and 39 were separated by HPLC (250/10 Nucleosil 100–7 C$_6$H$_5$; Acetonitrile: water+0.1% formic acid=40:60).

EXAMPLE 38

(Compound IIa14, $R_1$=Me, $R_2$=H, $R_3$=Me, $\alpha$=(R) Stereochemistry, *=(L) Stereochemistry, n=6):

mpt: 99.0–100.0° C. HPLC: Ret. Time: 52.6 min. $^1$H-NMR (in CD$_3$OD [=3.30 ppm], 16 mg/ml, 300 MHz, Room temp.): 4.39 (dd, J=8.4, 4.8, 1H), 2.38 (m, 3H), 2.15 (m, 1H), 1.94 (m, 1H), 1.59 (m, 1H), 1.28 (br., 25H), 1.10 (d, J=6.9, 3H), 0.89 (t, J=6.6, 3H). $^{13}$C-NMR (in CD$_3$OD [=49,0 ppm], 16 mg/ml, 75 MHz, Room temp.): 179.81, 176.95, 176.10, 53.51, 41.98, 35.36, 33.04, 31.54, 30.75 (2C), 30.73 (3C), 30.69 (2C), 30.63, 30.42, 28.60, 28.22, 23.67, 18.18, 14.36.

EXAMPLE 39

(Compound IIa15, $R_1$=Me, $R_2$=H, $R_3$=Me, $\alpha$=(S) Stereochemistry, *=(L) Stereochemistry, n=6):

mpt: 131.0–133.0° C. HPLC: Ret. Time: 55.6 min. $^1$H-NMR (in CD$_3$OD [=3.30 ppm], 15 mg/ml, 300 MHz, Room temp.): 4.38 (dd, J=8.4, 4.8, 1H), 2.37 (m, 3H), 2.15 (m, 1H), 1.95 (m, 1H), 1.60 (m, 1H), 1.28 (br., m, 25H), 1.10 (d, J=6.9, 3H), 0.89 (t, J=6.6, 3H). $^{13}$C-NMR (in CD$_3$OD [=49.0 ppm], 15 mg/ml, 75 MHz, Room temp.): 179.89, 177.05, 175.99, 53.51, 41.97, 35.36, 33.04, 31.54, 30.74 (7C), 30.63, 30.43, 28.44, 28.25, 23.68, 18.35, 14.36. mpt: 131.0–133.0° C. HPLC: Ret. Time: 55.6 min.

BIOLOGICAL ACTIVITY OF CRUDE AND PURIFIED HMP EXTRACTS, THE SYNTHETIC NATURAL HMP AND ITS DERIVATIVES

Experimentation provided evidence that there is cross-recognition of the HMP between seven Anastrepha species (*bezzii, leptozona, ludens, obliqua, serpentina, striata, suspensa*) and one species of a closely related genus of economic importance (*Toxotrypana curvicauda*). Of importance here, is the fact that these seven species responded to the *A. ludens* natural HMP described in this patent (see TABLE 2). Furthermore, our results indicate that *A. obliqua* also responds to a synthetic *A. ludens* pheromone derivative compound (described as example No. 29, compound). All these facts provide clear evidence that the general chemical structure of the HMP of all Anastrepha species must be homologous and that one general formula will suffice to deter oviposition in all Anastrepha species.

Methods Used

Electrophysiological Bioassays

These tests were conducted in the electrophysiology laboratory of the Swiss Federal Research Station at Wädenswil, Switzerland. Procedures and techniques used were developed by Städler and co-workers for studies with *Rhagoletis cerasi* (Städler et al. 1992). No modification was made to this technique. Basically, the stimulatory (biological) effect of HMP on the test flies was tested with the chemoreceptors located at specific hairs of the fly's tarsi.

Laboratory Bioassays

We followed a slightly modified version of the bioassays described by Boller and Aluja (1992). Instead of using fresh fruit as oviposition substrates, we utilized green 2.5 cm diam agar spheres wrapped in parafilm. We placed 30 such spheres on glass vials (12 mm diam and 60 mm height) (one sphere per vial). Vials were inserted into previously drilled holes in a 27×27×2 cm wooden board. Final arrangement of agar balls was hexagonal and distance between balls was ca. 1.5 cm (see Boller and Aluja (1992) for further details). The wooden board was transferred into a 40×30×30 cm Plexiglas cage, where we had placed mango leaves on the cage walls (to provide ample resting sites for flies). One afternoon previous to testing, 16 mated and gravid females were released into such a cage (containing food and water), and allowed them to oviposit into clean agar spheres. The next morning, ca. one hour previous to testing, we removed the wooden board with agar spheres.

The bioassays consisted of introducing a freshly prepared bioassay arena (wooden board with agar spheres) into a cage with flies (kept as described above) that we re allowed to oviposit during one hour into the spheres that were either clean or treated with HMP.

Out of the 30 spheres exposed to the flies, 15 balls were untreated (controls) and 15 treated, whereby the distribution of treated and untreated spheres was systematic.

During the experimental period of 60 min the test flies were continuously observed, and their landings, oviposition attempts or successful ovipositions on treated or untreated spheres, recorded. Every time a control or treated sphere was oviposited and marked, it was immediately replaced by an identical one of the same treatment.

With this information on successful ovipositions we computed a discrimination coefficient based on the following formula (Boller and Hurter 1985):

$$DC = \frac{A-B}{A+B} \times 100$$

Where A=ovipositions into untreated (control) spheres.

B=ovipositions into HMP treated spheres.

The DC can vary between −100 and +100. A DC of −100 would indicate that all eggs were laid into treated oviposition substrates. No difference between test substance and control would produce a DC of zero and hence no deterrent effect was achieved. A DC of +100 would indicate that not eggs were laid into treated oviposition substrates and hence an absolute deterrent effect was achieved.

Field Tests

Tests were conducted under natural conditions in tropical plum (*Spondias purpurea*), and mango (*Mangifera indica*) orchards. These tests consisted of applying *A. ludens* natural pheromonal extracts (100 mg/ml of MeOH extract diluted in water up to 10 mg/ml) with a knapsack sprayer to fruit trees visited by flies stemming from mid-sized local populations. Using the same method, we also applied example 29 of TABLE 3 (synthetic derivative of the *A. ludens* HMP; 100 ppm) to single fruit-bearing branches of *S. purpurea* trees visited by *A. obliqua* females, and example 37 of TABLE 3 (synthetic derivative of the *A. ludens* HMP; 50 ppm) to single fruit-bearing branches (and associated branchlets) of *Mangifera indica* visited by *A. obliqua* females (*A. ludens* and *A. serpentina* were also observed visiting fruits).

Results

Activity of Crude HMP Extracts

Methanol extracts elicited strong electrophysiological and behavioral responses in both laboratory and field bioassays. The results are summarized in TABLE 2 and show clearly that the HMP produced by 4 different Anastrepha species is perceived by *A. ludens* and *A. obliqua*, respectively, and support our findings in other laboratory bioassays involving 3 test species and their HMPs. In the case of *T. curvicauda* we were able to demonstrate (in electrophysiological tests and laboratory bioassays) that its HMP (contained in feces extracts), is recognized by *A. ludens* and *A. obliqua* (TABLE 2).

Activity of Natural *A. Ludens* HMP and Derivatives

Both the synthetic natural HMP and several of its derivatives elicited strong electrophysiological and behavioral responses in the laboratory (TABLE 3). Furthermore, the synthetic compound described as example No. 29 (compound IIa5) and compound described as example No. 37 (compound IIa13), also proved effective at significantly reducing oviposition by *A. obliqua* under field conditions (TABLE 3, last column).

TABLE 2. Biological activity of crude methanol extracts of natural host marking pheromone produced by *A. bezzii* (AB), *A. leptozona* (ALZ) *A. ludens* (AL), *A. obliqua* (AO), *A. serpentina* (AS), *A. suspensa* (ASU), *A. striata* (AST), *Toxotrypana curvicauda* (TC) and tested with females of *A. ludens, A. obliqua* and *A. serpentina*. C (=KCl) refers to the control substances used.

| | Electrophysiology and field test | | | | | | |
|---|---|---|---|---|---|---|---|
| | Electrophysiology Spikes per msec. | | | | | | Field test Efficacy % (Abbott) |
| Concentration of extract | 1.0 mg/ml MeOH | | | | | | 10 mg/ml |
| Test species | A. ludens | | | | | | A. obliqua |
| HMP origin | AO | ASU | AL | AS | TC | C(=KCl) | AL |
| Result | 99 | 91 | 91 | 93 | 89 | 5 | 84.7% |

| Laboratory bioassay | | | | | | | |
|---|---|---|---|---|---|---|---|
| Laboratory bioassay HMP origin and Discrimination coefficient DC 100 mg/ml MeOH | | | | | | | |
| Test species | AO | AL | AS | AST | ALZ | AB | TC |
| A. ludens | 100 | 100 | 82.9 | 79.4 | 79.6 | 100 | 88.6 |
| A. obliqua | 93.1 | 100 | 95.3 | 77.8 | — | 75.5 | 91.3 |
| A. serpentina | 100 | 100 | 100 | — | — | — | — |

Activity of Natural Pheromone and Derivatives

Results are summarized in TABLE 3. The data show pronounced biological activity in compounds described as examples 25, 29, 37, 38, 39, respectively.

TABLE 3. Biological activity of compounds of formula (IIa). Electrophysiology and behavioral laboratory tests were performed with A. ludens females using artificial hosts (agar spheres wrapped in parafilm). Field tests were carried out on *Spondias purpurea* (Tropical plum) and *Mangifera indica* (Mango) trees naturally infested by A. obliqua.

What is claimed is:

1. A compound 2-(2',14'-Dimethyl-pentadecanoylamino)-pentanedioic acid of the formula (I)

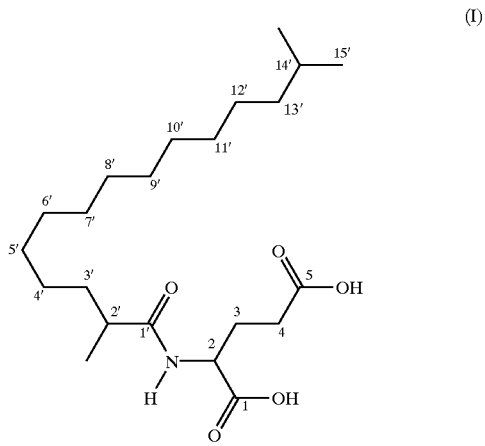

(I)

in the form of one of its optical isomers or their mixtures, and alkali metal, alkali earth metal, and ammonium mono- or di-carboxylic acid salts, that exhibit oviposition deterring activity in fruit flies of the genus Anastrepha.

2. A biopesticidal composition comprising the compound of claim 1 as an active ingredient, either in free form, or in the form of an agrochemically acceptable salt, and at least one adjuvant.

3. The composition of claim 2, wherein active ingredients are contained in quantities between 0.1 and 99% by weight of the final product.

TABLE 3

Biological activity of compounds of formula (IIa). Electrophysiology and behavioral laboratory tests were performed with A. ludens females using artificial hosts (agar spheres wrapped in parafilm). Field tests were carried out on *Spondias purpurea* (Tropical plum) and *Mangifera indica* (Mango) trees naturally infested by A. obliqua.

| | | Formula | | | | | Biological Activity | | |
|---|---|---|---|---|---|---|---|---|---|
| | | | | | | | Electro-physiology 1 ppm | Behavioral Laboratory Test | Field Tests Efficacy % |
| Test Compound | | R1 | R2 | R3 | * | n | α | Spikes/msec | 100 ppm DC | (Abbott) |
| (25) IIa1 | natural HMP | Me | Me | Me | L | 5 | R | 76 | 82.3 | — |
| (28) | natural HMP | Me | Me | Me | D | 5 | R | 50 | 23.2 | — |
| (26) IIa2 | | Me | Me | Me | SL | 5 | S | 16 | — | — |
| (27) IIa3 | | Me | Me | Me | D | S | S | 6 | — | — |
| (29) IIa5 | | Me | H | Me | L | 5 | R | 78 | 84.8 | 64.37 (100 ppm, plum) |
| (30) IIa6 | | Me | H | Me | D | 5 | R | 23 | — | — |
| (33) IIa9 | | H | Me | Me | L | 5 | — | 25 | 23.7 | — |
| (35) IIa11 | | H | H | Me | L | 5 | — | 12 | 8.3 | — |
| (38) IIa14 | | Me | H | Me | L | 6 | R | — | 84.3 | — |
| (39) IIa15 | | Me | H | Me | L | 6 | S | — | 61.7 | — |
| (37) IIa13 | | Me | H | Me | L | 6 | R/S | — | 78.4 | 77.15 (50 ppm, mango) |

4. A compound of formula (II):

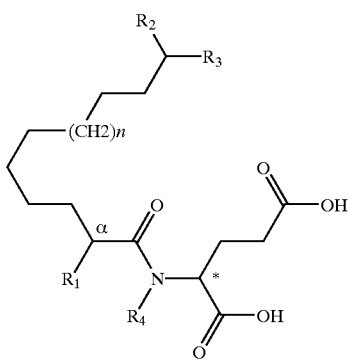

where $R_1$ is $C_1$–$C_4$ alkyl, $C_3$–$C_6$ cycloalkyl, $C_3$–$C_4$ alkenyl, $C_3$–$C_4$ alkynyl; $R_2$ and $R_3$ independent of one another are H, $C_1$–$C_4$ alkyl, $C_3$–$C_6$ cycloalkyl, $C_3$–$C_4$ alkenyl, $C_3$–$C_4$ alkynyl, benzyl, or benzyl which is substituted once to three times on the phenyl ring by halogen, $C_1$–$C_4$ alkyl;

$R_4$ is H or $C_1$–$C_4$ alkyl, $C_3$–$C_6$ cycloalkyl, $C_3$–$C_4$ alkenyl, $C_3$–$C_4$ alkynyl, $C_1$–$C_4$ alkyl carbonyl, benzyl or benzyl which is substituted once to three times on the phenyl ring by halogen, C1–$C_4$ alkyl, where α refers to (R) or (S) stereoisomers or a mixture of R and S stereoisomers; with the proviso that R1 is not=H;

where n=an integer between 0 and 15; and where * refers to the (L) or (D) amino acid stereochemistry or mixtures of (L) and (D) stereoisomers.

5. A compound of claim 4, wherein $R_1$ is Methyl, $R_2$ is H, $R_3$ is Me, $R_4$ is H, and n is 5.

6. A compound of claim 4, wherein $R_1$ is Methyl, $R_2$ is H, $R_3$ is Me, $R_4$ is H and n is 6.

7. A process for the preparation of a compound of formula II as claimed in claim 4, comprising:

reacting an activated acyl compound of the formula (III)

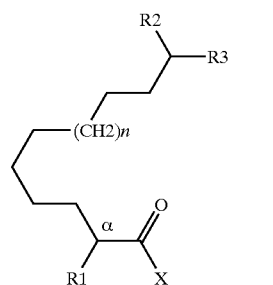

with a compound of the formula (VI)

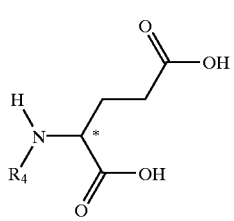

where $R_1$ is $C_1$–$C_4$ alkyl, $C_3$–$C_6$ cycloalkyl, $C_3$–$C_4$ alkenyl, $C_3$–$C_4$ alkynyl; $R_2$ and $R_3$ are independent of one another are H or $C_1$–$C_4$ alkyl, $C_3$–$C_6$ cycloalkyl, $C_3$–$C_4$ alkenyl, $C_3$–$C_4$ alkynyl benzyl, or benzyl which is substituted once to three times on the phenyl ring by halogen, $C_1$–$C_4$ alkyl; and X is a leaving group, $R_4$ is H or $C_1$–$C_4$ alkyl; $C_3$–$C_6$ cycloalkyl, $C_3$–$C_4$ alkenyl, $C_3$–$C_4$ alkynyl, $C_1$–$C_4$ alkyl carbonyl, benzyl or benzyl which is substituted once to three times on the phenyl ring by halogen, $C_1$–$C_4$ alkyl, where α refers to R or S or mixtures of their stereoisomers, with the proviso that R1 is not=H, and n is an integer between 0 and 15;

where * refers to (L) or (D) or mixtures of amino acid stereochemistry, in an inert solvent in the presence of a base and a solubilizing agent.

8. A process for the preparation of a compound of claim 4, comprising:

reacting an activated acyl compound of the formula (III)

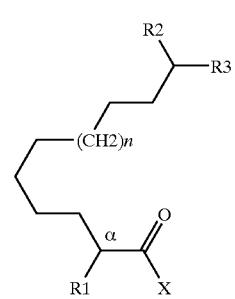

with a compound of the formula (IV)

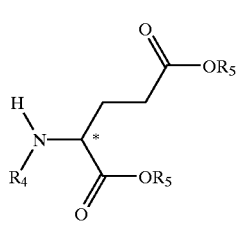

where $R_1$ is $C_1$–$C_4$ alkyl, $C_3$–$C_6$ cycloalkyl, $C_3$- or $C_4$ alkenyl, $C_3$- or $C_4$ alkynyl; $R_2$ and $R_3$ are independent of one another and are H or $C_1$–$C_4$ alkyl, $C_3$–$C_6$ cycloalkyl, $C_3$–$C_4$ alkenyl, $C_3$–$C_4$ alkynyl, benzyl or benzyl which is substituted once to three times on the phenyl ring by halogen, $C_1$–$C_4$ alkyl; and X is a leaving group;

$R_4$ is H or $C_1$–$C_4$ alkyl, $C_3$–$C_6$ cycloalkyl, $C_3$–$C_4$ alkenyl, $C_3$–$C_4$ alkynyl, $C_1$–$C_4$ alkyl carbonyl, benzyl or benzyl which is substituted once to three times on the phenyl ring by halogen, $C_1$–$C_4$ alkyl;

where α refers to (R) or (S) or mixtures of their stereoisomers; with the proviso that R1 is not=H;

where n=an integer between 0 and 15, where * refers to (L) or (D) or mixtures of (L) and (D) amino acid stereochemistry;

in an inert solvent in the presence of a base and a solbilizing agent, to give a compound (V)

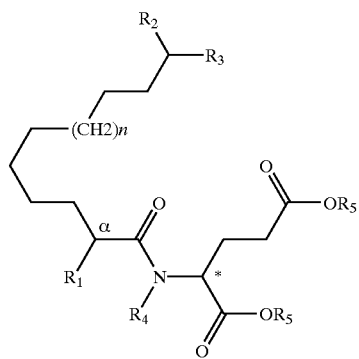

(V)

which can be converted to compounds of formula I and II by replacing $R_5$ groups with hydrogen.

9. A procedure to protect agricultural crops against infestation by Anastrepha species comprising the application of an adequate amount comprised of between 0.1 g to 200 g of a compound according to claim 1 to the surface of the crop to be protected.

10. A procedure to protect agricultural crops against infestation by Anastrepha species comprising the application of an adequate amount comprised of between 0.1 g to 200 g of a compound according to claim 4 to the surface of the crop to be protected.

11. A method of producing a biopesticidal composition as described in claim 2, in which the active ingredient is intimately mixed with the adjuvants.

12. A method for controlling fruit flies of the genus Anastrepha which comprises applying a biopesticidal composition of claim 3 to fruit flies of the genus Anastrepha or to their locus.

13. A pesticidal composition comprising at least one compound of formula (II) according to claims 4, 5 or 6 as active ingredient, either in free form, or in the form of an agrochemically acceptable salt, and at least one adjuvant.

14. A method of producing a pesticidal composition as described in claim 13, in which the active ingredient is intimately mixed with the adjuvants.

15. A method for controlling fruit flies of the genus Anastrepha which comprises applying a composition of claim 13 to fruit flies of the genus Anastrepha or to their locus.

* * * * *